(12) United States Patent
Jin et al.

(10) Patent No.: US 11,179,428 B2
(45) Date of Patent: Nov. 23, 2021

(54) *DUNALIELLA* MUTANT AND METHOD FOR PRODUCING PIGMENT BY USING SAME

(71) Applicant: INDUSTRY-UNIVERSITY COOPERATION FOUNDATION HANYANG UNIVERSITY, Seoul (KR)

(72) Inventors: Eon Seon Jin, Seoul (KR); Min Jae Kim, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 325 days.

(21) Appl. No.: 16/306,477

(22) PCT Filed: May 31, 2017

(86) PCT No.: PCT/KR2017/005685
§ 371 (c)(1),
(2) Date: Nov. 30, 2018

(87) PCT Pub. No.: WO2017/209510
PCT Pub. Date: Dec. 7, 2017

(65) Prior Publication Data
US 2019/0290712 A1 Sep. 26, 2019

(30) Foreign Application Priority Data
Jun. 1, 2016 (KR) .......................... 10-2016-0068217

(51) Int. Cl.
*C12N 1/12* (2006.01)
*A61K 36/05* (2006.01)
(Continued)

(52) U.S. Cl.
CPC .............. *A61K 36/05* (2013.01); *A23K 10/16* (2016.05); *A23K 20/179* (2016.05); *A23L 5/46* (2016.08);
(Continued)

(58) Field of Classification Search
CPC ..................................................... C12N 1/125
See application file for complete search history.

(56) References Cited

FOREIGN PATENT DOCUMENTS

| CN | 101597569 B | 1/2011 |
| KR | 10-2006-0060039 A | 6/2006 |
| KR | 10-2010-0081388 A | 7/2010 |

OTHER PUBLICATIONS

Eonseon Jin, et al., "A Mutant of the Green Alga *Dunaliella salina* Constitutively Accumulates Zeaxanthin Under All Growth Conditions", Biotechnology and Bioengineering, Jan. 5, 2003, pp. 115-124, vol. 81, No. 1.
(Continued)

*Primary Examiner* — Rosanne Kosson
(74) *Attorney, Agent, or Firm* — Sughrue Mion, PLLC (57) ABSTRACT

A novel alga mutant having improved pigment productivity is provided. The mutant can be used to produce carotenoid-based pigments, particularly, xanthophyll by using a small amount of energy, and thus can effectively produce pigment on an industrial level. In addition, the mutant can be used as a source for foods, health functional foods, and medications which contain a pigment. Further, when account is taken of the physiological characteristics of the euryhaline microalgae *Dunaliella* and the geological characteristics of Korean, the three sides of which are in contact with the sea, sea-water can be used as a culture medium, with the expectation of reducing the cost and leading to the development of related industries.

15 Claims, 9 Drawing Sheets

Specification includes a Sequence Listing.

(51) Int. Cl.
*A23K 20/179* (2016.01)
*A23K 10/16* (2016.01)
*A23L 5/46* (2016.01)
*A23L 33/10* (2016.01)
*A61K 31/047* (2006.01)
*C12P 23/00* (2006.01)
*C12R 1/89* (2006.01)

(52) U.S. Cl.
CPC ............ *A23L 33/10* (2016.08); *A61K 31/047* (2013.01); *C12N 1/12* (2013.01); *C12N 1/125* (2021.05); *C12P 23/00* (2013.01); *A23V 2002/00* (2013.01); *C12R 2001/89* (2021.05)

(56) References Cited

OTHER PUBLICATIONS

Hector Mendoza, et al., "Characterization of Dunaliella salina strains by flow cytometry: a new approach to select carotenoid hyperproducing strains", Electronic Journal of Biotechnology, Oct. 15, 2008, 13 pages, vol. 11, No. 4.
International Search Report for PCT/KR2017/005685 dated Sep. 8, 2017 [PCT/ISA/210].

| mg/g | Day14 | |
|---|---|---|
| | Zea1 | MP3 |
| Zeaxanthin | 5.94 | 8.30 |

SEQUENCE LISTING

<160> NUMBER OF SEQ ID NOS: 4

<210> SEQ ID NO 1
<211> LENGTH: 19
<212> TYPE: DNA
<213> ORGANISM: Artificial
<220> FEATURE:
<223> OTHER INFORMATION: ITS1-F primer

<400> SEQUENCE: 1
tccgtaggtg aacctgcgg                                              19

<210> SEQ ID NO 2
<211> LENGTH: 20
<212> TYPE: DNA
<213> ORGANISM: Artificial
<220> FEATURE:
<223> OTHER INFORMATION: ITS1-R primer

<400> SEQUENCE: 2
gctgcgttct tcatcgatgc                                             20

<210> SEQ ID NO 3
<211> LENGTH: 20
<212> TYPE: DNA
<213> ORGANISM: Artificial
<220> FEATURE:
<223> OTHER INFORMATION: ITS2-F primer

<400> SEQUENCE: 3
gcatcgatga agaacgcagc                                             20

<210> SEQ ID NO 4
<211> LENGTH: 20
<212> TYPE: DNA
<213> ORGANISM: Artificial
<220> FEATURE:
<223> OTHER INFORMATION: ITS2-R primer

<400> SEQUENCE: 4
tcctccgctt attgatatgc                                             20

DUNALIELLA MUTANT AND METHOD FOR PRODUCING PIGMENT BY USING SAME

CROSS-REFERENCE TO RELATED APPLICATION

This application is a National Stage of International Application No. PCT/KR2017/005685, filed on May 31, 2017, which claims priority to and the benefit of Korean Patent Application No. 10-2016-0068217 filed on Jun. 1, 2016, the disclosure of which is incorporated herein by reference in its entirety.

BACKGROUND

1. Field of the Invention

The present invention relates to algae having a pigment-producing ability, a pigment composition including the same, and a method of producing the pigment.

2. Discussion of Related Art

Macular degeneration is a disease which may result in visual impairment caused by degeneration of the macula, which is nerve tissue located in the center of the inside of the retina of an eye. The macula is the place where most photoreceptor cells gather, and since the image of an object is also the center of the macula, the macula plays a very important role in visual acuity. The most common cause of macular degeneration may be aging (age-related macular degeneration), and is known to be related to family history, race, and smoking. Since the macula is responsible for the central vision, when degeneration occurs in the manula, distorted vision in the form of metamorphopsia, vision loss and central scotoma appear. Macular degeneration is largely classified into non-exudative (dry) macular degeneration and exudative (wet) macular degeneration. While the non-exudative macular degeneration mostly has no influence on visual acuity except for late stage retinal and choroidal atrophies, and has yellow deposits called drusen in the macula, the exudative macular degeneration in which subretinal hemorrhage, subretinal fluid, and pigment epithelial detachment appear has decreased visual acuity since the position of such a lesion is under or in direct contact with the macula at an early stage. The exudative macular degeneration accounts for approximately 10 to 20% of the total cases of macular degeneration, and if the exudative macular degeneration is left untreated, visual acuity decreases quickly and leads to blindness within two years after diagnosis in most cases. To prevent macular degeneration, it is important to detect macular abnormalities early by a regular funduscopic examination and reduce controllable factors such as obesity, smoking, high blood pressure, etc. Smoking damages choroidal circulation such that blood antioxidant materials are reduced and choroidal vasoconstriction occurs, resulting in hypoxic damage, and therefore, patients at risk of macular degeneration must quit smoking. In addition, since a macular pigment (lutein or zeaxanthin) serves to reduce age-induced damage to keep the macula healthy, it can help prevent macular degeneration by eating enough vegetables and fruits or taking commercially available vitamins.

Macular pigments reduce aging-induced decreased visual acuity occurring in the central region of the retina and prevent damage to retinal tissue by bright light, and a representative example of this pigment is an oxycarotenoid pigment, called xanthophyll, which is included in the carotenoid group and produced by oxygenation of the carotenoid. Xanthophylls include lutein and zeaxanthin. Lutein is an antioxidant which protects the inside of eyes damaged by oxygen-free radicals naturally occurring in the body, and is known to kill cancer cells by suppressing the growth of blood vessels supplying tumors and have some effects in the prevention of breast cancer, colon cancer, lung cancer and ovarian cancer and skin cancer. Animals cannot produce xanthophylls, and thus can only be obtained by intake of food. These xanthophylls are present in the leaves, flowers and fruits of plants, along with chlorophylls and carotenes. Recently, health functional foods for eye health including xanthophylls are attracting attention.

As raw material of zeaxanthin and lutein, conventionally, marigold flower petals have been used, and extraction of these pigments from other higher plants have also been studied. Moreover, zeaxanthin and lutein are also produced in bacteria by genetically modifying pigment synthesis mechanisms. Studies have also been carried out to obtain these pigments from microalgae. Among these conventionally-used raw materials, marigold flower petals have disadvantages in that it takes a long time to raise plants for production, and the production costs are high because productivity is not large compared with a land area for production.

To solve these problems, there has been an attempt to develop zeaxanthin- and lutein-producing algae into which a pigment synthesis mechanism using a bacterial system replacing a higher plant system is inserted, but the pigments obtained from bacteria are ultimately determined as inappropriate to be used as food additives. In addition, since, in Korea, genetically modified organisms (GMOs) using gene insertion technology are not preferred, such bacteria-grown pigments have a fatal drawback in the food additive market where consumers' awareness is important, and high costs are required for bacterial culture media, maintenance of a bioreactor, etc., as well for a higher plant system.

In the case of the method of obtaining these pigments from microalgae, conventional microalgae are wild type, not modified. They contain a certain amount of lutein, but very low amounts of zeaxanthin according to an amount of light, and therefore they have limitations in use for optimal production.

Accordingly, there is a continuing demand for the development of methods of producing or replacing raw materials for food.

SUMMARY OF THE INVENTION

The present invention is directed to providing a raw material which can replace a xanthophyll conventionally used as a raw material for food or a method that can replace a conventional method of producing a raw material, and specifically, a microorganism with an excellent xanthophyll-producing ability, particularly, an excellent ability to produce lutein and zeaxanthin, a composition including the same, and a method of producing a xanthophyll using the same.

To attain the above-mentioned object, the inventors had tried to develop algae which can increase the productivity of wild-type or existing microalgae using mutagenesis, rather than genetic recombination which can cause a problem in the food industry, and developed a mutant having higher macular pigment productivity than conventional *Dunaliella* sp. algae and a method of producing an optimal pigment using the same. Therefore, the present invention was completed.

In one aspect, the present invention provides *Dunaliella* sp. Macular Pigment 3 (MP3) (KCTC 12990BP) algae.

The *Dunaliella* sp. MP3 algae may have a xanthophyll-producing ability.

The *Dunaliella* sp. MP3 algae may have the ability to produce one or more pigments selected from the group consisting of lutein and zeaxanthin; chlorophyll b, chlorophyll a and β-carotene.

In another aspect, the present invention provides a culture of *Dunaliella* sp. MP3 (KCTC 12990BP) algae.

In still another aspect, the present invention provides a pigment composition including one or more selected from the group consisting of *Dunaliella* sp. MP3 (KCTC 12990BP) algae, a culture of the algae, a dried product of the culture, and an extract of the culture.

In yet another aspect, the present invention provides a composition for oral administration, which includes one or more selected from the group consisting of *Dunaliella* sp. MP3 (KCTC 12990BP) algae, a culture of the algae, a dried product of the culture, and an extract of the culture.

In yet another aspect, the present invention provides a composition for feed or a feed additive, which includes one or more selected from the group consisting of *Dunaliella* sp. MP3 (KCTC 12990BP) algae, a culture of the algae, a dried product of the culture, and an extract of the culture.

In yet another aspect, the present invention provides a composition for food or a food additive, which includes one or more selected from the group consisting of *Dunaliella* sp. MP3 (KCTC 12990BP) algae, a culture of the algae, a dried product of the culture, and an extract of the culture.

In yet another aspect, the present invention provides a method of producing a pigment, which includes culturing *Dunaliella* sp. MP3 (KCTC 12990BP) algae.

In yet another aspect, the present invention provides a method of producing a raw material of food or feed, which includes culturing *Dunaliella* sp. MP3 (KCTC 12990BP) algae.

In yet another aspect, the present invention provides a method for strengthening or maintaining eye health; preventing or improving macular degeneration; preventing or improving function degradation of eye; improving or preventing damage to the retina; suppressing aging; maintaining retinal health; reducing a risk of the occurrence of macular degeneration; or preventing or improving decreased visual acuity of a subject, comprising administering one or more selected from the group consisting of *Dunaliella* sp. MP3 (KCTC 12990BP) algae according to claim 1, a culture of the algae, a dried product of the culture, and an extract thereof to the subject.

Large amounts of zeaxanthin and lutein can be produced using a mutant of the present invention with low energy, and thus zeaxanthin and lutein can be effectively produced and provided on an industrial level. The composition of the present invention can be applied as raw materials of food, health functional food and medications which contain zeaxanthin and lutein pigments. Further, considering the physiological characteristics of euryhaline microalgae *Dunaliella* and the geological characteristics of Korea, which has three sides of which are in contact with sea, sea water can be used as a culture medium, and thus it is expected to reduce production costs and development of related industries.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

However, the present invention can be modified and implemented in various forms, and therefore, only specific embodiments will be described in detail. Also, the present invention is not limited to specific disclosures, and it should be understood that the present invention includes all modifications, equivalents and alternatives included in the technical idea and scope of the present invention.

Hereinafter, the present invention will be described in further detail.

The present invention relates to *Dunaliella* sp. MP3 (KCTC 12990BP) algae.

The *Dunaliella* sp. algae are unicellular green algae with two flagella of equal length, their cells are spindle-shaped, their size is 7 to 25 µm in length depending on the species and has a chloroplast. The *Dunaliella* sp. algae can be grown in an environment with a high salt concentration.

The mutant is constructed by general mutagenesis, and identified by isolation using subculture and a conventional method. The mutagenesis may be performed using a general mutagen, and in one exemplary embodiment of the present invention, the mutation is induced by treatment of a chemical.

The *Dunaliella* MP3 mutant of the present invention has a pigment-producing ability, and specifically, a xanthophyll-producing ability. More specifically, the *Dunaliella* MP3 mutant has the ability to produce lutein and zeaxanthin, and may further produce one or more selected from the group consisting of chlorophyll b, chlorophyll a and β-carotene.

The mutant has a significantly higher capability of producing zeaxanthin per cell than conventional wild-type *Dunaliella* sp. algae, and has 20 to 30% higher zeaxanthin accumulation per cell than base algae *Dunaliella* sp. Zea1 (*BIOTECHNOLOGY AND BIOENGINEERING*, VOL. 81, NO. 1), and therefore it can be effectively used as algae for producing a xanthophyll.

In one exemplary embodiment, since it was confirmed that the MP3 mutant of the present invention has the highest zeaxanthin accumulation per unit cell density and per dry weight compared to the wild-type and Zea1 algae of the same species (FIG. 6B), it was found that the mutant of the present invention has a very high mycological characteristic such as a high ability of producing a xanthophyll, particularly, zeaxanthin, and thus it was confirmed that the mutant can be effectively used as a production source of the xanthophyll pigment.

The mutant of the present invention can survive under dim light, and specifically, can be cultured under a light intensity ranging from 10 to 2,000 µmol photons/m$^2$s. The mutant cannot be photosynthesized under complete darkness below a dim light condition, and cells can get damaged by light stress under a very high light condition. When the mutant is cultured under the above-described conditions, the xanthophyll content in the mutant may be increased, and an excellent growth rate may be exhibited.

Figure 6A:
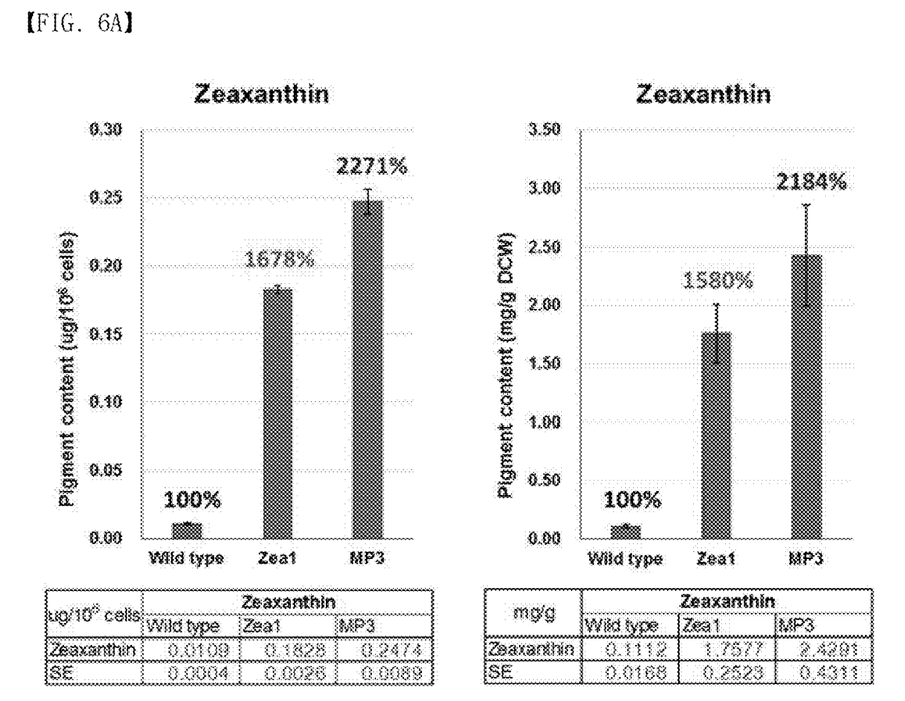
FIG. 6A is a set of HPLC graphs for comparing amounts of zeaxanthin contained in the wild-type *Dunaliella* sp. algae, Zea1 and the MP3 mutant by measuring pigment contents in the cells harvested on the second day after culture under the light intensity of 100 μmol photons/m²s. (A) shows the zeaxanthin contents (μg) per $1 \times 10^6$ cells, and (B) shows the zeaxanthin contents (mg) per 1 g of dry cell weight.
Figure 6B:
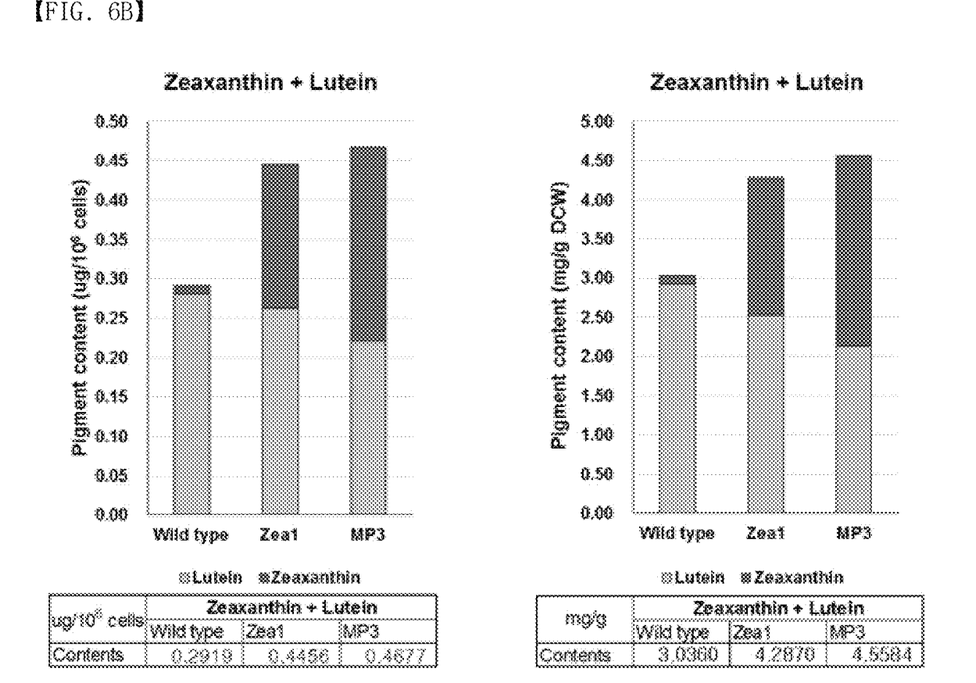
FIG. 6B shows graphs of comparing zeaxanthin and lutein levels contained in the wild-type *Dunaliella* sp. algae, Zea1 and the MP3 mutant by measuring a pigment content through HPLC after culture for 2 days at a light intensity of 100 μmol photons/m²s and harvesting. (A) shows zeaxanthin and lutein contents (μg) per $1 \times 10^6$ cells, and (B) shows zeaxanthin and lutein contents (mg) 1 g of dry cell weight.

The MP3 mutant may be properly grown under a conventional growth environment for the *Dunaliella* sp. algae (light intensity, temperature, salinity, etc.). In addition, since the MP3 mutant has excellent zeaxanthin accumulation at a low light intensity (FIG. 6), due to a high xanthophyll-producing ability, it can be industrially effectively used as xanthophyll pigment-producing microorganisms, has a relatively lower density in a group under a high light intensity compared to other algae, and thus has an excellent pigment production efficiency by photosynthesis in single cells. Specifically, the MP3 mutant has a zeaxanthin content per cell approximately 40% or more higher than that of the Zea1 algae, which are known as a conventional zeaxanthin-improving strain.

The MP3 mutant may be cultured in a sea water environment, and specifically, in a culture medium containing sea water. The mutant of the present invention may be cultured under a salinity condition ranging from 0.05M to 5.5M based on a NaCl concentration. The culture medium may further include Tris, as well as NaCl. The culture medium contains nutrients necessary for microorganisms to be cultured, that is, to culture a specific microorganism, and further contains a material used for a specific purpose. The medium is called a growth medium or culture medium, and is a concept encompassing a natural medium, a synthetic medium and a selective medium. The *Dunaliella* mutant may be cultured according to a conventional culture method. In one exemplary embodiment, it was confirmed that the MP3 mutant of the present invention had an excellent zeaxanthin-producing ability in the culture medium composition environment of Table 1.

The pH of the culture medium is not particularly limited as long as the *Dunaliella* sp. algae can survive and grown, and the *Dunaliella* sp. algae may survive at pH 6 or more, specifically, at pH 7 to pH 9, and may have the optimal growth rate in a range from pH 8.0 or more to less than pH 9.0.

The MP3 mutant is developed by a chemical mutation using *Dunaliella* sp. Zea1 (*BIOTECHNOLOGY AND BIOENGINEERING*, VOL. 81, NO. 1) as base algae, and identified as the *Dunaliella* sp. Algae through ITS sequencing.

Figure 8A:
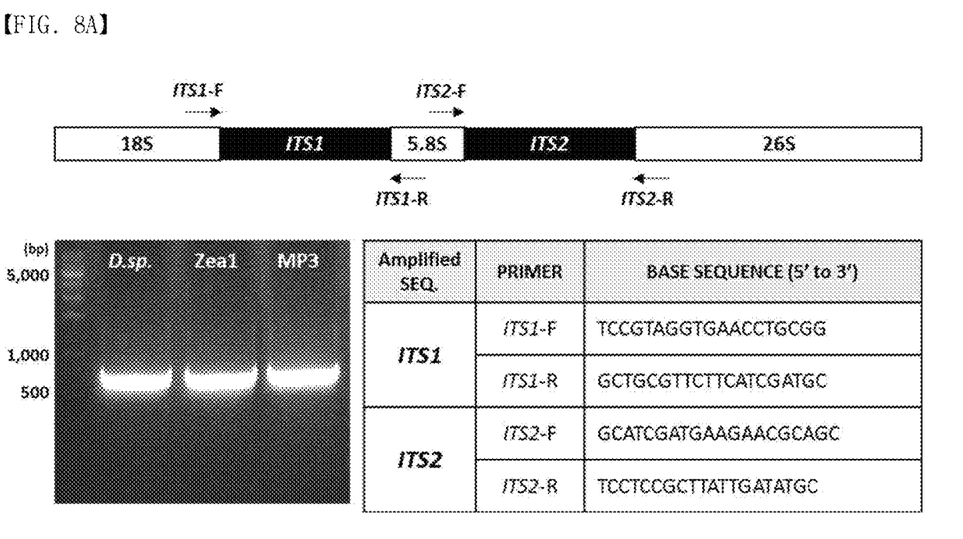
FIG. 8A is the PCR result using primer information and ITS1-F and ITS2-R primers to identify a *Dunaliella* sp. strain.
Figure 8B:
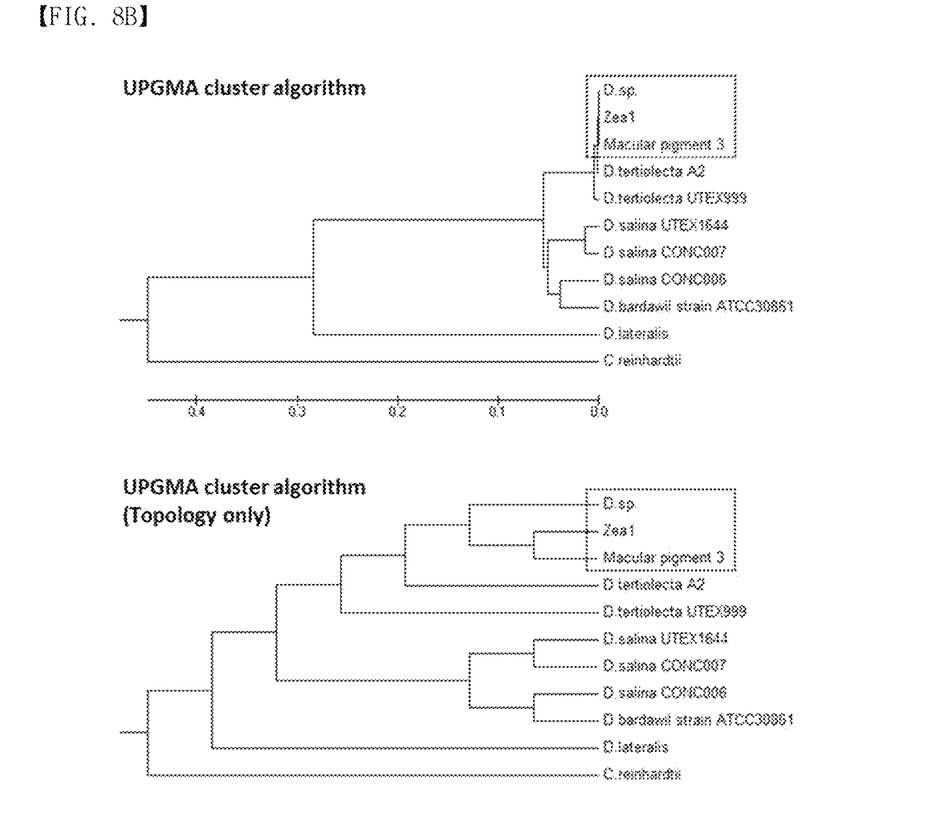
FIG. 8B is the phylogenetic analysis of *Dunaliella* sp. strains.

Specifically, using ITS1 (ITS1-F: TCCGTAGGT-GAACCTGCGG, ITS1-R: GCTGCGTTCTTCATC-GATGC) and ITS2 (ITS2-F: GCATCGAT-GAAGAACGCAGC, ITS2-R: TCCTCCGCTTATTGATATGC) as primers for amplifying a base sequence, the results of ITS1 and ITS2 sequencing for the *Dunaliella* strains (wild-type, Zea1 and base algae) and the mutant MP3 were summarized and aligned using the clustalW program, and then a phylogram is constructed using an unweighted pair group method with arithmetic mean (UPGMA) algorithm in the MEGA6 program (FIG. 8B).

From a topological point of view, when looking at the phylogram, it was confirmed that the mutant of the present invention is close to the base algae Zea1, and both are close to the wild-type *Dunaliella* species. In addition, it can be confirmed that the mutant of the present invention is phylogenetically related to *Dunaliella tertiolecta* A2.

Based on the analysis result, the selected mutant of the present invention was named *Dunaliella* sp. MP3, and deposited under the Budapest Treaty on the International Recognition of the Deposit of Microorganisms for the Purpose of Patent Procedure in in Korean Collection for Type Cultures (KCTC) at Korea Research Institute of Bioscience and Biotechnology (KRIBB) of 125 Gwahak-ro, Yuseong-gu, Daejeon 305-806, Republic of Korea on Mar. 16, 2016 and received Accession No. KCTC 12990BP on Mar. 23, 2016.

High contents of pigments, particularly, xanthophyll-based pigments may be accumulated in cells of the MP3 mutant of the present invention, and among these pigments, zeaxanthin may be contained at a higher amount, and therefore the MP3 mutant algae may be cultured to be effectively used as a raw material of food, feed, medications, etc.

In terms of this, the present invention relates to a culture of *Dunaliella* sp. MP3 (KCTC 12990BP) algae.

The "culture" used herein refers to a medium in which a specific microorganism is cultured, and in other words, a medium obtained after culture. The culture includes the *Dunaliella* sp. MP3. In addition, the culture includes all of a concentrated and dried product of the culture obtained by culturing and processing such as concentrating and drying the culture medium. The culture may include a by-product of the culture, and a type of the culture may be, but is not limited to, a liquid or a solid.

The medium contains nutrients necessary for microorganisms to be cultured, that is, to culture a specific microorganism, and further contains a material used for a specific purpose. The medium is called a growth medium or culture medium, and is a concept encompassing a natural medium, a synthetic medium and a selective medium. The pH of the medium may be in a range in which the *Dunaliella* sp. MP3 algae can be grown, and for example, at pH 6 or more, and preferably, at pH 7 to pH 9.

In addition, the present invention relates to a composition including one or more selected from the group consisting of the *Dunaliella* sp. MP3 (KCTC 12990BP) algae of the present invention, a culture of the algae, a dried product thereof, and an extract thereof.

The composition may be used for improving human or animal health.

The mutant of the present invention produces xanthophyll-based pigments including zeaxanthin and lutein and then accumulates them in a body, and in terms of this, the composition may be a pigment composition or a xanthophyll pigment composition.

Figure 7A:
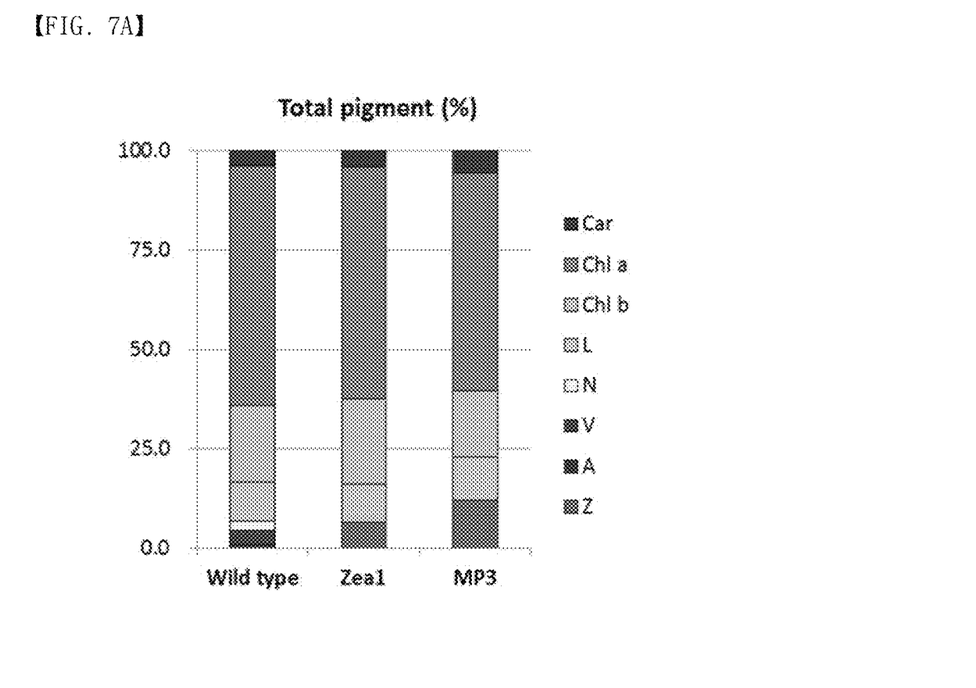
FIG. 7A is a graph showing pigment contents (wt %) in the total weight of the wild-type *Dunaliella* sp. algae, Zea1, and the MP3 mutant.

The pigment composition may include zeaxanthin at 10 wt % to 15 wt % with respect to the total content of the pigments included in the composition. According to an exemplary embodiment of the present invention, from a result of measuring the zeaxanthin content in the total pigment per cell of each of the *Dunaliella* wild-type algae, Zea1 algae and the MP3 mutant, it can be confirmed that the MP3 mutant has a significantly higher zeaxanthin content among the total pigments, than that of the wild-type and Zea1 (FIG. 7A).

The pigment composition may be used as a raw material of food or feed, or as a preparation for oral administration.

Therefore, the composition, or a pigment composition or xanthophyll pigment composition including an extract thereof may be a composition for oral administration since it can be included in food, medications or feed.

The composition for oral administration may be included in an oral preparation formulated by a method known in the art in the form of powder, granules, tablets, pills, sugar-coated tablets, capsules, a liquid, a gel, a syrup, a slurry or a suspension. For example, an oral preparation may be obtained as tablets or sugar-coated tablets by mixing an active ingredient with a solid excipient, grinding the mixture, adding suitable supplements and processing the resulting mixture into a granulated mixture. Examples of suitable excipients may include saccharides such as lactose, dextrose, sucrose, sorbitol, mannitol, xylitol, erythritol and maltitol, starches such as corn starch, wheat starch, rice starch and potato starch, celluloses such as cellulose, methyl cellulose, sodium carboxymethylcellulose and hydroxypropyl methyl-cellulose, and fillers such as gelatin, polyvinylpyrrolidone. In some cases, cross-linked polyvinylpyrrolidone, agar, alginic acid, or sodium alginate may be further added as a disintegrating agent.

In addition, since the composition may be added to food or feed to attain a specific purpose, in terms of this, the composition may be a food composition, a food additive composition, a feed composition or a feed additive composition. When the composition is used in feed or food, xanthophyll pigments, particularly, zeaxanthin and lutein, which are produced by the *Dunaliella* sp. MP3 algae and accumulated in cells can maintain or strengthen the health of the body. Specifically, the zeaxanthin and lutein are macular pigments and may prevent or improve macular degeneration, and thus are effective in prevention or improvement of macular degeneration-related eye diseases. More specifically, since the zeaxanthin and lutein are effective in strengthening or maintaining eye health; preventing or improving macular degeneration; preventing or improving eye functionality; improving or preventing damage to the retina; suppressing aging; maintaining retinal health; reducing a risk of the occurrence of macular degeneration; or preventing or improving decreased visual acuity, the feed or food composition may be used to prevent or improve the symptoms, or used for the above-mentioned effects.

The composition "for additives" used herein includes any component added to food or feed as well as a main ingredient, and specifically, may be an active ingredient having functionality in food or feed, or a food additive added for coloring, preservation, etc. to processed food, which is defined by the Ministry of Food and Drug Safety (MFDS).

The food may be a health functional food, more specifically, a health functional food for eye health.

The food, food additive, feed or feed additive composition may further include other active ingredients without damaging the activity of the *Dunaliella* sp. MP3 (KCTC 12990BP) algae of the present invention, a culture of the algae, a dried product thereof and an extract thereof. In addition, additional components including a carrier may be further included.

In the present invention, the feed composition may be prepared as fermented feed, compounded feed, or pellets or silage. The fermented feed may be prepared by including the *Dunaliella* sp. MP3 algae of the present invention, dry cells of the algae, a culture thereof and an extract thereof, and further including various microorganisms or enzymes. The compounded feed may be prepared by mixing various types of general feed with the *Dunaliella* sp. MP3 algae of the present invention, dry cells of the algae, a culture thereof and an extract thereof. The pellet-type feed may be prepared by formulating the fermented feed or compounded feed using a pelletizer. The silage may be prepared by mixing green forage with the *Dunaliella* sp. MP3 algae, dry cells of the algae, a culture of the algae and/or an extract thereof, and a use of the composition of the present invention is not limited thereto.

The composition may be prepared by being mixed with a carrier and a flavor, which are conventionally used in the food or pharmaceutical field, and administered in the form of a tablet, a troche, a capsule, an elixir, a syrup, a powder, a suspension or a granule. As the carrier, a binder, a lubricant, a disintegrating agent, an excipient, a solubilizing agent, a dispersing agent, a stabilizer or a suspending agent may be used. As an administration method, oral administration, parenteral administration or a coating method may be used, but oral administration is preferred. In addition, a dose may be suitably selected depending on the degree of absorption, inactivation rate, and excretion rate of an active ingredient in a body, the age, sex or condition of a subject. The pH of the composition can be easily adjusted according to conditions for preparing a drug or food containing the composition.

The composition may include any one selected from the group consisting of the *Dunaliella* sp. MP3 (KCTC 12990BP) algae, a culture of the algae, a dried product thereof and an extract thereof at 0.001 to 99.99 wt %, and preferably 0.1 to 99 wt % with respect to the total weight of the composition, and a content of the active ingredient may be suitably adjusted according to a method of using the composition, and an intended use of the composition.

The *Dunaliella* sp. MP3 (KCTC 12990BP) algae may be included in the composition as it is or in a dry form, and the algae culture may be included in the composition in a concentrated or dried form. In addition, the dried product refers to a dried form of the algae or a culture thereof, or a powder form prepared by lyophilization.

In addition, the extract refers to an extract obtained by extracting MP3 algae, a culture thereof or a dried product thereof, and includes an extract obtained using a solvent, and one obtained by disrupting the MP3 algae of the present invention. Specifically, the extract may be obtained by extracting and isolating pigments accumulated in cells of the *Dunaliella* sp. MP3 (KCTC 12990BP) algae of the present invention by a physical or chemical method.

The extraction process may be performed by a conventional method, and for example, a target pigment may be extracted by adding an extraction solvent to cells, homogenizing the cells, and disrupting the cells. After extraction, the algae lysate may be removed by centrifugation, and the extraction solvent may be removed by a method such as vacuum distillation. In addition, the extraction process may further include a conventional purification process. Since the pigment is insoluble in water, it may be more easily extracted from the algae of the present invention.

Since the *Dunaliella* MP3 mutant of the present invention has an excellent xanthophyll-producing ability, particularly, zeaxanthin at a low light intensity, the composition including the mutant and a by-product thereof is effective in improvement of body activity, maintenance of body functionality and prevention of degradation of body functionality. Specifically, the xanthophyll pigment is known to have a macular degeneration inhibitory effect, an antioxidant effect and an anticancer effect, and therefore, the composition of the present invention may be used as a raw material included in food, medications or feed to maintain body health, specifically, maintain a xanthophyll pigment-involved body function, or prevent or enhance degradation of the body function.

In addition, the present invention provides a method of producing a pigment using *Dunaliella* sp. MP3 (KCTC 12990BP) algae.

In addition, the present invention provides a method of producing a raw material of food or feed, which includes an operation of culturing *Dunaliella* sp. MP3 (KCTC 12990BP) algae.

When the *Dunaliella* sp. MP3 (KCTC 12990BP) algae of the present invention is used, the xanthophyll accumulation in the cultured *Dunaliella* algae may be increased, and thus the supply of a raw material industrially used may be effectively performed.

The production method may include an operation of culturing *Dunaliella* sp. MP3 (KCTC 12990BP) algae.

In addition, after the culturing operation, the production method may further include an operation of isolating the *Dunaliella* sp. MP3 algae of the present invention from the culture. The isolated algae may be further subjected to a processing operation including drying.

In addition, the production method may further include an operation of extracting a pigment from the *Dunaliella* sp. MP3 (KCTC 12990BP) algae, a culture of the algae, or a concentrated or dried product of the culture.

The culture may be performed in a medium under a salinity condition of 0.05M to 5.5M based on an NaCl concentration. In addition, the culture may be performed under a dim light condition, specifically, a light intensity condition in a range from 10 to 2,000 μmol photons/m$^2$s. Since the *Dunaliella* MP3 mutant of the present invention has an excellent pigment-producing ability even at a low light intensity, a xanthophyll content in a body may be increased, and a xanthophyll may be highly accumulated without supply of high intensity light energy, and thus this method can be effectively used on an industrial level.

The above-mentioned extraction may be performed by a conventional method of extracting a pigment from a microorganism, for example, an enzyme method, ultrasonic extraction, or mechanical extraction, but the present invention is not limited thereto.

In addition to the culturing operation, the production method may further include a concentrating operation for increasing a content of the algae after the culture, and a drying operation for further reducing moisture of the algae that has been subjected to the concentrating operation. However, the concentrating or drying operation is not needed, and is generally performed using concentrating and drying methods and machines, which are conventionally used in the art.

The production method may further include a purifying operation after the extracting operation, which may be performed by a conventional purification method used in the art.

The xanthophyll prepared through the concentration or drying operation may be used as a raw material of food, health functional food, cosmetics or drugs.

The method of producing a xanthophyll may be performed by employing a different method without impairing the effect of the present invention.

Contents of the algae and composition can also be applied to the production method of the present invention.

Hereinafter, preparation examples and experimental examples of the present invention will be described in detail. The following examples and experimental examples are merely provided to illustrate the present invention, but the scope of the present invention is not limited thereto.

EXAMPLE 1

Mutagenesis, Selection of Mutant and Analysis of Morphological Characteristic

High zeaxanthin-containing algae Zea1 (*Dunaliella* sp. Zea1) derived from *Dunaliella* sp. and used as base algae in this experiment were cultured in a liquid medium having the composition shown in Table 1 below. Shaking culture was performed under conditions including a light intensity of approximately 100 μmol photons/m$^2$s, a temperature of 25 to 26° C. and a speed of 90 rpm.

TABLE 1

| Component | Concentration in culture medium |
|---|---|
| Salts and major component | |
| NaCl | 1.5 M |
| Tris | 40 mM |
| KNO$_3$ | 5 mM |
| MgCl$_2$ | 4.5 mM |
| MgSO$_4$ | 0.5 mM |
| CaCl$_2$ | 0.3 mM |
| K$_2$HPO$_4$ | 0.1 mM |
| FeCl$_3$ | 0.002 mM |
| NaEDTA | 0.02 mM |

TABLE 1-continued

| Component | Concentration in culture medium |
|---|---|
| Trace component | |
| $H_3BO_3$ | 50 μM |
| $MnCl_2$ | 10 μM |
| $ZnSO_4$ | 0.8 μM |
| $CuSO_4$ | 0.4 μM |
| $NaMoO_4$ | 2 μM |
| $NaVO_3$ | 1.5 μM |
| $CoCl_2$ | 0.2 μM |
| Carbon source | |
| $NaHCO_3$ | 25 mM |
| pH of culture medium | 7.4 | base algae Zea1 were cultured until they reached the exponential phase, and then cells were harvested and resuspended to have a cell density of $8×10^6$ to $10×10^6$ cells/mL, and then treated with a chemical mutation-inducing material, ethyl methane sulfonate (EMS), to have a final concentration of 0.2 μM. After incubation for two hours, the treated EMS was washed with a liquid medium, and then the cells were harvested by centrifugation. The cells were resuspended with a liquid medium, incubated in the dark for one day, and then transferred to a solid medium in which agar is further added to the same composition as the liquid medium of Table 1 and plated thereon. After one week, colonies developed on the solid medium were isolated, and a single colony was transferred to the liquid medium of Table 1 and cultured in the liquid. A mutant was selected by analyzing the characteristic of each colony.

Specifically, by visual observation, pale green colonies, which looked lighter than the wild-type and base algae (Zea1), were first screened, and algae having a relatively higher zeaxanthin content were secondly screened by HPLC analysis of the first-selected colony of algae.

Figure 1A:
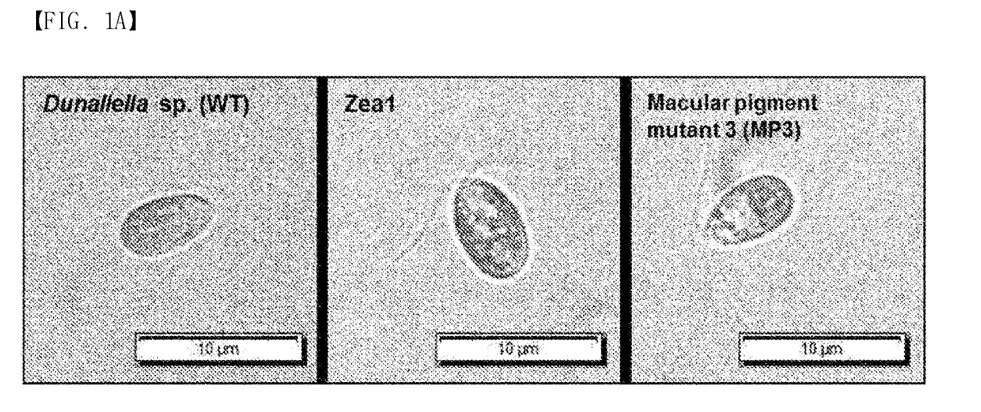
FIG. 1A is a set of microscope images (magnification: 1000×) of the mutant of the present invention, wild-type (WT) *Dunaliella* sp. algae, the base algae of the mutant of the present invention (Zea1), and an MP3 mutant. The bars in these images represent 10 μm.

To compare morphological characteristics of the mutants, microscope images of the wild-type *Dunaliella* sp. algae, the base algae Zea1 of the present invention and the MP3 mutant (macular pigment mutant 3, hereinafter, referred to as a mutant or MP3 mutant) obtained in the present invention are shown in FIG. 1A.

As shown in FIG. 1A, it was confirmed that, under the same light intensity condition, the *Dunaliella* sp. wild-type, Zea1 and the mutant algae were grown with a similar morphology, and it was confirmed that the mutant of the present invention has the same morphology as the wild-type algae and only has a difference in the brightness of a cell color.

Figure 1B:
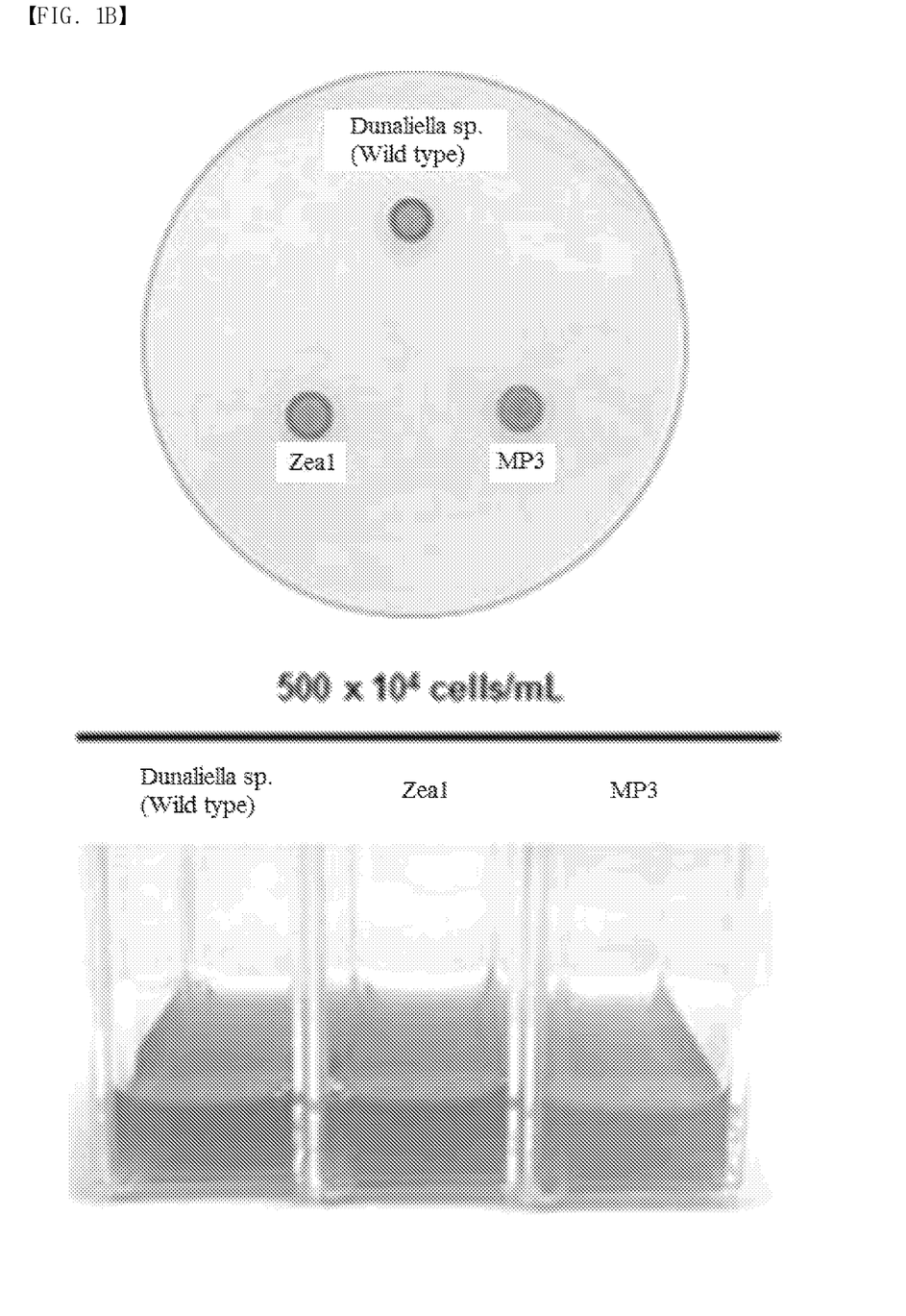
FIG. 1B is a set of images showing the culture state when the wild-type algae, Zea1 and the MP3 mutant are grown to the same cell density ($500 \times 10^4$ cells/mL). The upper image shows the culture state in an agar-containing solid medium, and the lower image shows the culture state in a liquid medium.

As shown in FIG. 1B, it was confirmed that the color of the mutant was lighter green and yellow than that of the wild-type *Dunaliella* sp. algae and Zea1, and in the liquid culture in the lower image, the color of the mutant also showed more lighter green and yellow.

Figure 2:
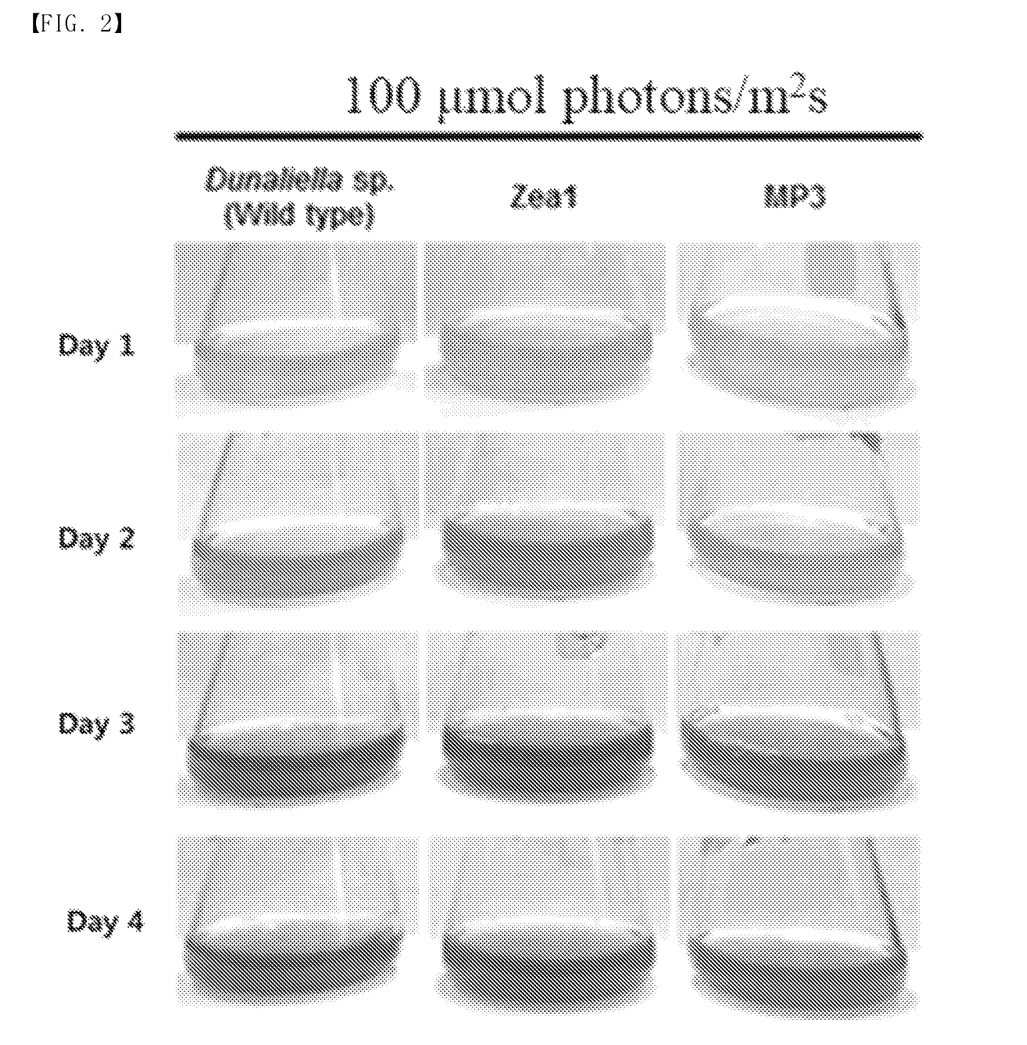
FIG. 2 is a set of images of flasks containing a liquid medium for comparing growth under a light intensity of 100 μmol photons/m²s.

In addition, as shown in FIG. 2, in the images of flasks containing liquid media cultured to compare growth under 100 μmol photons/$m^2$s, compared with the wild-type, the base algae of the present invention, Zea1, did not have a significant difference in growth rate, but compared with the wild-type and the Zea1 algae, the MP3 mutant did have a difference in color according to a density. It was understood that the above-described result is caused by a difference in growth rate from the wild-type and the Zea1 algae, and actually, as shown in FIG. 3 below, since the mutant of the present invention had 1 to 1.5-day difference in growth rate, compared with Zea1, it was confirmed that a color difference according to a density was shown even in the image.

EXAMPLE 2

Confirmation of Growth Characteristic of Isolated Mutant 2-1. Confirmation of Growth Rate To compare the cell growth rates and the final growth levels of the wild-type *Dunaliella* algae, Zea1 and the MP3 mutant, each type of algae was inoculated in a medium of the composition shown in Table 1 at a cell density of $1×10^6$ cells/mL, and cultured at different light intensities of 50, 100 and 300 μmol photons/$m^2$s. In the comparative experiment, the temperature was 25 to 26° C., and shaking culture was performed at 90 rpm. After the initiation of culture, 0.5 mL of the culture was taken and a cell density per mL was measured on day 1, 2, 3, 4 or 5 under a microscope using a hemocytometer. The cell density according to a light intensity was measured on each measuring day, and the result is shown in FIG. 3.

Figure 3:
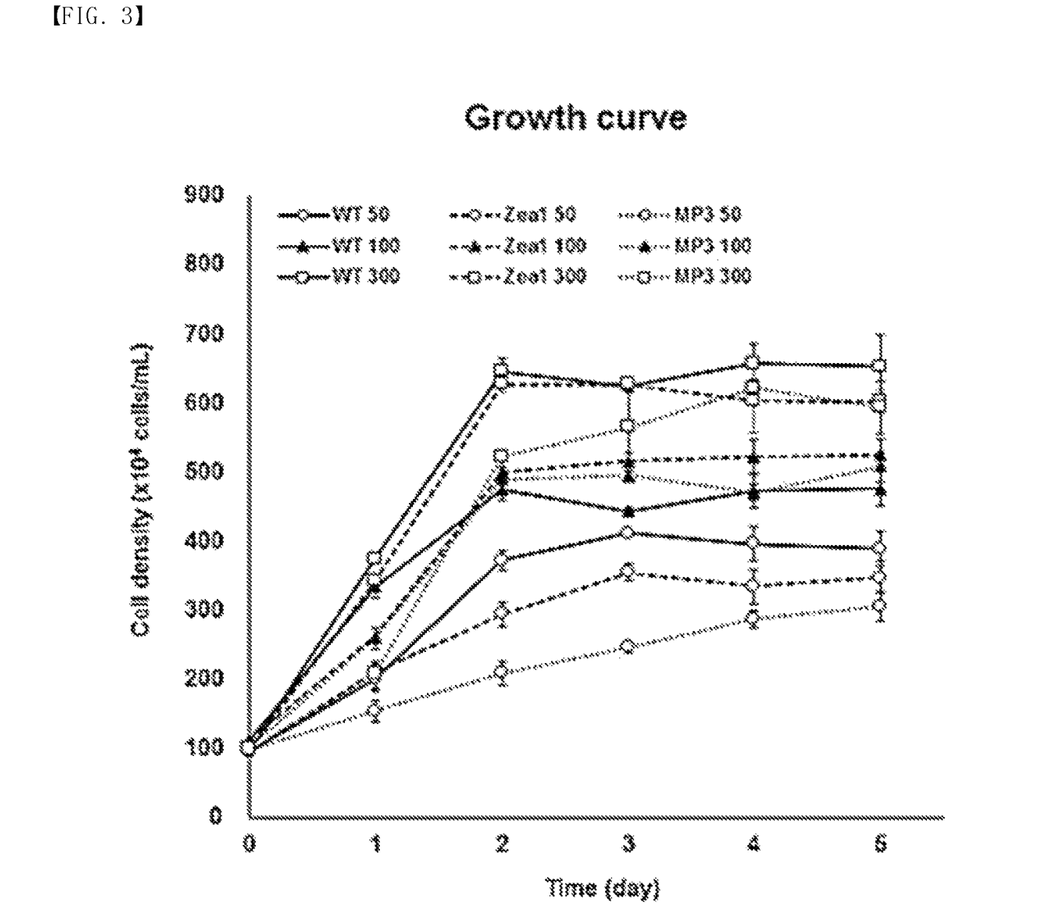
FIG. 3 is a graph showing the patterns of increasing cell densities of the wild-type *Dunaliella* sp. algae, Zea1, and the MP3 mutant of the present invention. The horizontal axis indicates culture time (day), the vertical axis indicates cell density ($\times 10^4$ cells/mL), and the numbers represent a light intensity with each group was treated (units: μmol photons/m²s).

As shown in FIG. 3, the MP3 mutant had a smaller increase in cell density than the wild-type and Zea1 as the culture period passed. As a result of comparing the time to reach the same cell density, it was confirmed that the wild-type algae had a growth rate approximately 1 to 1.5 days faster than the MP3 mutant, but the final cell density reached a similar level.

2-2. Measurement of Dry Weight

Actually, to use microalgae on an industrial level, since a dry cell weight is also an important part, dry weights were measured to compare the final biomass thereof.

Specifically, samples were inoculated at $100×10^4$ cells/mL, and harvested on day 2, which is in the exponential phase. To compare the final algal biomass, 1 mL or 2 mL of the suspension of the culture was filtered through a microfilter (filter paper), the filtrate was dried in a dry oven at 65° C. for 24 hours, and then $1×10^6$ cells of the wild-type, Zea1 and the mutant were weighed to measure dry cell weights. Since *Dunaliella* was grown in a high-salinity liquid medium, residual salts remain after the cells were harvested by centrifugation and can affect the dry cell weight of the cells. For this reason, the experiment was performed while the filtrate was filtered through a filter paper to remove as many salts as possible. The result is shown in FIG. 4A.

Figure 4A:
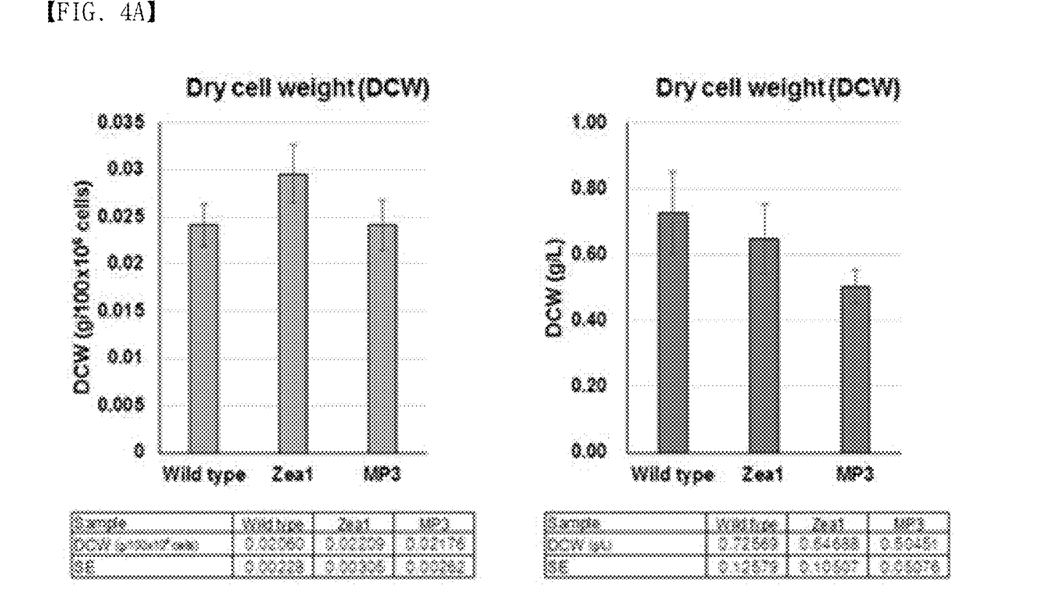
FIG. 4A is a set of graphs showing the dry cell weights (g) of the wild-type algae, Zea1 and the MP3 mutant per $100 \times 10^4$ cells.
Figure 4B:
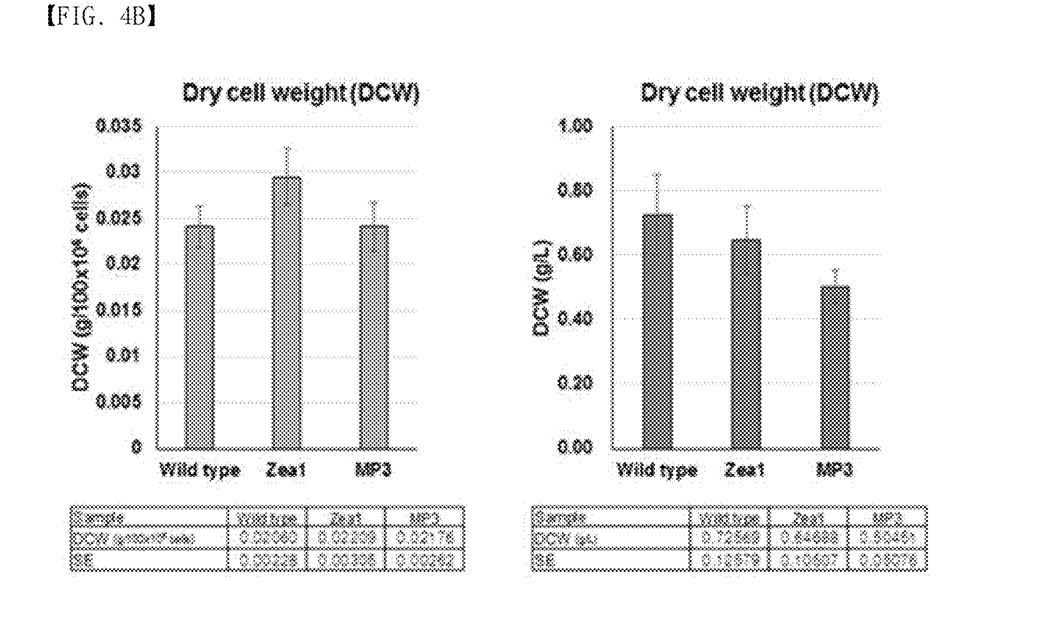
FIG. 4B is a set of graphs of measuring biomass as the dry cell weights (g) per liter (L) of the wild-type algae, Zea1 and the MP3 mutant.

In addition, a dry cell weight was calculated in each of 0.5, 1 and 2 mL of the culture, and thereby a trend line was plotted to compare the value with the dry cell weight in the 1 L of the culture (FIG. 4B).

As shown in FIG. 4A, it was confirmed that there was a difference in dry cell weight per liter in proportion to cell density. It was confirmed that the dry cell weight per cell density was the highest in the Zea1 algae, and the dry cell weight per liter was the highest in the wild-type *Dunaliella* algae. Therefore, under the same light intensity condition, it was seen that the growth and the proliferation rate of the mutant of the present invention are lower than those of the wild-type and the Zea1 algae. In the case of algae, when there are too many cells forming colonies, a transmittivity of light through the cells is lower and thus the rate of photosynthesis may be decreased. When the mutant of the present invention has a high pigment content per unit cell or dry cell weight, it is expected to be more suitable as pigment-producing algae, and an experiment of confirming a pigment content was performed.

EXAMPLE 3

Pigment Analysis of Mutant

Single colonies were isolated from colonies developed after the treatment of a mutagenesis material and continuously cultured, and then pigment analysis was performed by HPLC for each colony.

Specifically, the isolated single colonies were cultured in a liquid medium under a condition of 100 µmol photons/m$^2$s for 5 days, and specific conditions were the same as those used in Example 1. Pigments were extracted from the harvested algal cells using 80% acetone, and the supernatant obtained by centrifugation was re-filtered through a nylon filter and then analyzed by HPLC.

Specifically, for pigment extraction, the total flow rate of a solvent was 1.2 mL per minute, from 0 minute to 15 minutes, Tris (pH 8.0) was 14%, acetonitrile was uniformly decreased from 84% to 0%, and methanol and ethyl acetate were 2% in the beginning and increased to 68% and 32%, respectively, up to 15 minutes. Afterward, for 3 minutes (from 15 minutes to 18 minutes), the above-mentioned ratio of the solvents was maintained, and then a post-run was performed for 1 minute (from 18 minutes to 19 minutes) with the initial ratio of the solvents and carried out for another 6 minutes. A pump was LC-20A Prominence (Shimadzu), a column was Waters Spherisorb™ S5 (DS1 4.6×250 mm, 5 µm Cartridge Column, USA), and a column temperature was maintained at 40° C. Data analysis was performed by a photodiode array detector (SPD-M20A, Shimadzu), and concentrations of carotenoid pigments including zeaxanthin detected at 445 nm and chlorophyll a detected at 670 nm were determined using a standard curve quantifying zeaxanthin and chlorophyll a, which were purchased from DHL (Agern Alle, Horsholm, Denmark).

Figure 5:
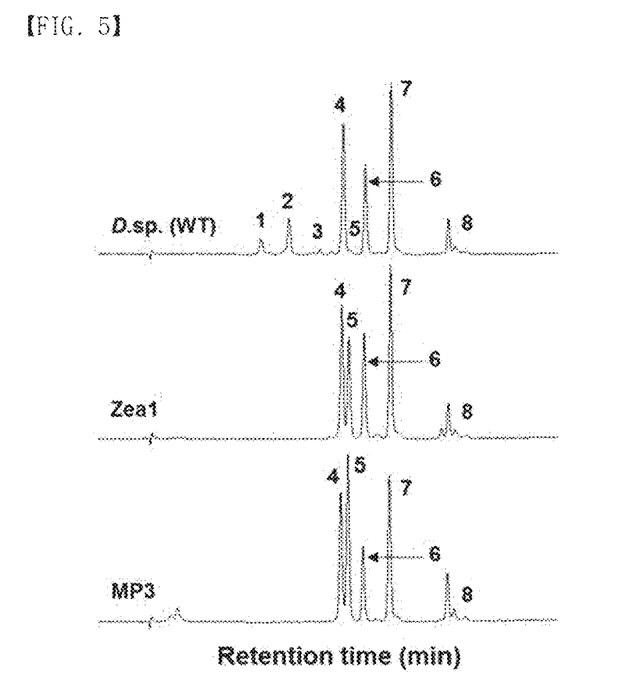
FIG. 5 is a set of HPLC analysis graphs showing pigment profiles for the wild-type *Dunaliella* sp. algae, Zea1 and the MP3 mutant (1: neoxanthin, 2: violaxanthin, 3: antheraxanthin, 4: lutein, 5: zeaxanthin, 6: chlorophyll b, 7: chlorophyll a, and 8: β-carotene).

FIG. 5 shows HPLC analysis graph showing pigment profiles in respective algae, and FIG. 6 shows a set of graphs quantitatively analyzing zeaxanthin and lutein contents of respective algae grown under 100 µmol photons/m$^2$s using a chromatogram.

In addition, on day 2 (the point of time at which the algae reached the stationary phase) after the culture in 100 mL of a culture medium in 250 mL flasks under a light intensity of 100 µmol photons/m$^2$s, algae grown to a cell density of 1×10$^6$ or algal cells were harvested from the culture, and then on the basis of 1 g dry cell weight (DCW), a comparison result of zeaxanthin contents is shown in FIG. 6A, and a comparison result of zeaxanthin and lutein contents is shown in FIG. 6B. The pigment content per DCW was calculated by dividing a value (mg/1×10$^6$ cells) obtained by dividing a pigment content (mg/L) obtained by HPLC by cell density (1×10$^6$ cells/ml) per mL by a dry cell weight per 1×10$^6$ cells (mg/1×10$^6$ cells).

As shown in FIG. 5, it was confirmed that the MP3 mutant of the present invention has a higher zeaxanthin peak (no. 5) than the wild-type algae and the base algae Zea1. In addition, although Zea1 is a zeaxanthin-accumulating mutant, it can be seen that the mutant of the present invention has a higher zeaxanthin-producing ability when compared thereto.

As shown in FIGS. 6A and 6B, under the same culture conditions, the MP3 mutant included at least a 20-fold increased accumulation of zeaxanthin compared to the wild-type, and approximately 40% or more increased accumulation of zeaxanthin compared to the base algae Zea1. Therefore, it can be seen that the MP3 mutant of the present invention had a considerably higher zeaxanthin-producing ability than a conventional *Dunaliella* genus.

EXAMPLE 4

Confirmation of Zeaxanthin-Producing Ability in Isolated Mutant

An amount of zeaxanthin accumulated in a mutant isolated by quantitative analysis by visual observation and HPLC was compared with that accumulated in the base algae (Zea1).

Compared with the wild-type *Dunaliella* algae and the base algae (Zea1) algae, the mutant grown under the same light intensity condition (100 µmol photons/m$^2$s) did not have a great difference in size (FIG. 1A), but as shown in FIG. 1B, when cells were inoculated at 500×10$^4$ cells/mL in a solid medium and a liquid medium, the MP3 mutant appeared yellow, compared with the wild-type. Accordingly, it can be confirmed by visual observation that, in the mutant of the present invention, under a relatively low light intensity of 100 µmol photons/m$^2$s, zeaxanthin was continuously accumulated, and as this light intensity condition does not generally require much energy, it demonstrates that a desired product can be obtained with less energy and high efficiency.

Particularly, although having a lower growth rate, the mutant of the present invention had a higher zeaxanthin content accumulated in algae per unit cell density under the same light intensity condition than the wild-type and the Zea1 algae, which indicates that the mutant can be used as xanthophyll-producing algae with much higher efficiency than the conventional xanthophyll-producing algae. Therefore, an experiment was performed to confirm whether the ability to produce zeaxanthin accumulated in the mutant of the present invention can be maintained after the culture.

To confirm a zeaxanthin-producing ability in the mutant, 1×10$^6$ cells/mL were inoculated in 500 mL of a culture medium and cultured. Light intensity and shaking culture conditions are the same as described above. After inoculation, the cells were incubated for 14 days (11 to 12 days after reaching the stationary phase), and then harvested, followed by measuring the zeaxanthin content in the total pigments. The result is shown in FIGS. 7A and 7B.

Figure 7B:
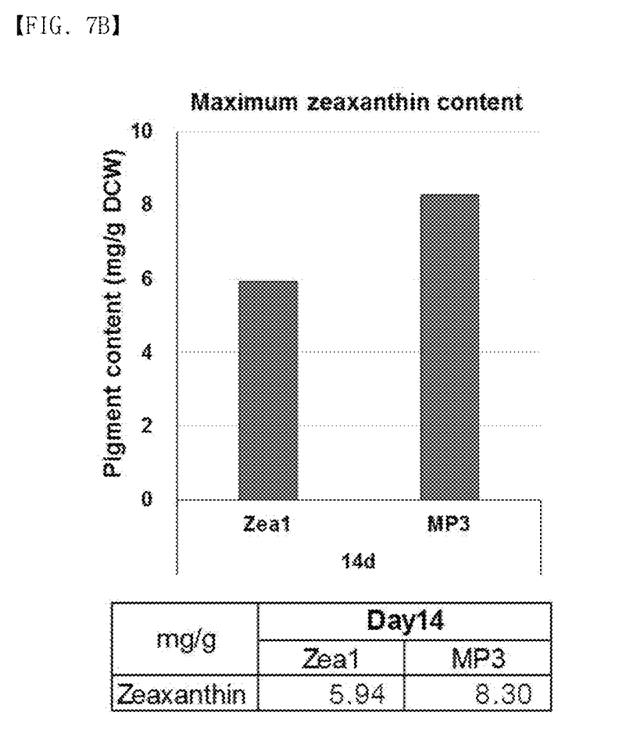
FIG. 7B is a graph showing the zeaxanthin content (mg/g DCW) per 1 g of dry cell weight of Zea1 or the MP3 mutant cultured for 14 days.

As shown in FIGS. 7A and 7B, it can be confirmed that the zeaxanthin productivity of the mutant of the present invention (MP3) was 8.3 mg/g DCW, which is 30% or more higher than 6 mg/g DCW of the conventional base algae Zea1. When the mutant of the present invention (MP3) was compared with the wild-type and the base algae Zea1, it can be confirmed that the zeaxanthin content of the total pigments was very high, and the zeaxanthin productivity per dry cell weight was also considerably higher than that of the conventional base algae Zea1. Therefore, it was confirmed that the MP3 mutant of the present invention has a considerably superior zeaxanthin-producing ability.

EXAMPLE 5

Phylogenetic Analysis of Isolated Mutant

For phylogenetic analysis of the MP3 mutant of the present invention screened in Example 1, a microorganism was identified by sequencing of an ITS gene.

Specifically, for ITS sequencing, a PCR product of the ITS gene amplified by PCR was subjected to electrophoresis (FIG. 8A), and the amplified part was cut from the agarose gel to isolate DNA using a gel extraction kit (Cosmo Genetech Co., Ltd.), and then sequencing was performed at Macrogen.

The analyzed sequences were aligned with ITS genes of some *Dunaliella* strains registered at NCBI (http://www.ncbi.nlm.nih.gov/). First, the ITS sequence of each strain was aligned to each other using the clustalW program, and a phylogenetic tree was built from the aligned sequences using an unweighted pair group method with arithmetic mean (UPGMA) algorithm in the MEGA6 program to perform comparative analysis of a phylogenetic relationship. At this time, the *Dunaliella* ITS sequence which was subjected to comparison was obtained from the NCBI gene bank, and details are as follows (in parentheses, gene bank code): *D. tertiolecta* A2 (U66956), *D. tertiolecta* UTEX999 (AF313434, AF313435), *D. salina* UTEX1644 (AF313428, AF313429), *D. salina* CONC006 (AF313424, AF313425), *D. salina* CONC007 (AF313426, AF313427), *D. bardawil* strain ATCC30861 (AF313430, AF313431), *D. lateralis* (AF313444, AF313445), and *C. reinhardtii* (U66954).

As shown in FIG. 8B, from a topological point of view, it was confirmed that the mutant of the present invention is included in *Dunaliella* sp., MP3 is close to the base algae Zea1, both of which are close to the wild-type *Dunaliella* sp. and phylogenetically linked to *Dunaliella tertiolecta* A2. Therefore, it was confirmed that the mutant of the present invention is a very closely related species with respect to *Dunaliella tertiolecta* genetically.

Based on this, the screened mutant of the present invention was identified as *Dunaliella* sp., named *Dunaliella* sp. MP3, and granted accession number KCTC 12990BP from the Korean Collection for Type Cultures (KCTC) of the Korea Research Institute of Bioscience and Biotechnology (KRIBB).

The invention claimed is:

1. An isolated *Dunaliella* sp. Macular Pigment 3 (MP3) (KCTC 12990BP) alga having a xanthophyll-producing ability.

2. The isolated alga according to claim 1, wherein the *Dunaliella* sp. MP3 (KCTC 12990BP) alga has an ability to produce:
   lutein and zeaxanthin; and
   one or more pigments selected from the group consisting of chlorophyll b, chlorophyll, a and β-carotene.

3. A purified culture of *Dunaliella* sp. MP3 (KCTC 12990BP) alga.

4. A pigment composition, comprising:
   one or more selected from the group consisting of the *Dunaliella* sp. MP3 (KCTC 12990BP) alga according to claim 1, a culture of the alga, a dried product of the culture and an extract thereof.

5. The pigment composition according to claim 4, which comprises zeaxanthin at 10 to 15 parts by weight with respect to 100 parts by weight of total pigments of the pigment composition.

6. A composition for oral administration, comprising:
   one or more selected from the group consisting of the *Dunaliella* sp. MP3 (KCTC 12990BP) alga according to claim 1, a culture of the alga, a dried product of the culture, and an extract thereof.

7. A feed or feed additive composition, comprising:
   one or more selected from the group consisting of the *Dunaliella* sp. MP3 (KCTC 12990BP) alga according to claim 1, a culture of the alga, a dried product of the culture, and an extract thereof.

8. A food or food additive composition, comprising:
   one or more selected from the group consisting of the *Dunaliella* sp. MP3 (KCTC 12990BP) alga according to claim 1, a culture of the alga, a dried product of the culture, and an extract thereof.

9. The A composition comprising one or more selected from the group consisting of the *Dunaliella* sp. MP3 (KCTC 12990BP) algae according to claim 1, a culture of the algae, a dried product of the culture, and an extract thereof, wherein the composition is effective in strengthening or maintaining eye health; improving macular degeneration; improving function degradation of eye;
   improving damage to the retina; suppressing aging; maintaining retinal health;
   reducing a risk of the occurrence of macular degeneration; or improving decreased visual acuity.

10. A method of producing a pigment, comprising:
    culturing the *Dunaliella* sp. MP3 (KCTC 12990BP) alga of claim 1 to an amount sufficient to produce the pigment.

11. The method according to claim 10, further comprising:
    extracting the pigment from the *Dunaliella* sp. MP3 (KCTC 12990BP) alga.

12. The method according to claim 10, wherein the pigment is a xanthophyll pigment.

13. A method of producing a raw material for food or feed, comprising: culturing the *Dunaliella* sp. MP3 (KCTC 12990BP) alga of claim 1 to an amount that is sufficient to make the raw material for adding to the food or feed.

14. A method for strengthening or maintaining eye health; improving macular degeneration; improving function of the eye; improving damage to the retina; suppressing aging;
    maintaining retinal health; reducing a risk of the occurrence of macular degeneration; or improving decreased visual acuity in a subject in need thereof, comprising administering to the subject a therapeutically effective amount of a composition comprising one or more selected from the group consisting of the *Dunaliella* sp. MP3 (KCTC 12990BP) Alga according to claim 1, a culture of the alga, a dried product of the culture, and an extract thereof to the subject.

15. The method of claim 10, further comprising the steps of:
    a) concentrating and/or drying the algal culture; and
    b) extracting the pigment from the concentrated and/or dried algal culture.

* * * * *